United States Patent [19]

Hilsen

[11] Patent Number: 5,611,355
[45] Date of Patent: Mar. 18, 1997

[54] SNORING AND SLEEP APNEA DEVICE

[76] Inventor: Kenneth L. Hilsen, 55 North Ave., Fort Lee, N.J. 07024

[21] Appl. No.: 416,431

[22] Filed: Mar. 31, 1995

Related U.S. Application Data

[63] Continuation of Ser. No. 75,801, Jun. 14, 1993, abandoned.

[51] Int. Cl.$^6$ .................................................. A61F 5/56
[52] U.S. Cl. .................................................. 128/848
[58] Field of Search ....................... 128/848, 859–862; 433/6

[56] References Cited

U.S. PATENT DOCUMENTS

| | | | |
|---|---|---|---|
| 2,705,492 | 4/1955 | Chandler | 128/862 |
| 3,997,162 | 12/1976 | Scullin | 273/DIG. 30 |
| 4,055,895 | 11/1977 | Huge . | |
| 4,173,219 | 11/1979 | Lentine | 128/861 |
| 4,304,227 | 12/1981 | Samelson . | |
| 4,396,373 | 8/1983 | Dellinger | 433/6 X |
| 4,505,672 | 3/1985 | Kurz | 433/6 |
| 4,901,737 | 2/1990 | Toone . | |
| 5,035,613 | 7/1991 | Breads et al. . | |
| 5,037,295 | 8/1991 | Bergersen | 433/6 |
| 5,055,039 | 10/1991 | Abbatte et al. | 433/6 |
| 5,082,007 | 1/1992 | Adell | 128/862 |
| 5,145,364 | 9/1992 | Martz et al. | 433/6 |
| 5,277,202 | 1/1994 | Hays | 128/848 |
| 5,313,960 | 5/1994 | Tomasi | 128/848 |
| 5,365,945 | 11/1994 | Halstrom | 128/848 |

FOREIGN PATENT DOCUMENTS 254918  2/1988  Germany .............................. 128/848

OTHER PUBLICATIONS

Carl J. Drago, Tarnish & Corrosion with the use of intraoral magnets, The Journal of Prosthetic Dentistry, vol. 66., No. 4, pp. 536–540, Oct. 1991.

O. T. Altay et al. The biological effects of omplanted magnetic fileds on the bone tissue of dogs, The Inter. Journal of Oral & Maxiloofacial impacts., vol. 6, #3, pp. 345–349, 1991.

Primary Examiner—Jessica Harrison
Assistant Examiner—Michael O'Neill
Attorney, Agent, or Firm—Stephen E. Feldman

[57] ABSTRACT

A device which can be molded to fit a particular user's mouth for the prevention of snoring and sleep apnea, comprises upper and lower mounting members and a releasable fastening assembly. The upper mounting member is substantially U-shaped and has a front face, a rear face and upper and lower surface portions. The upper surface portions are adapted to be engaged with the upper dentitions of the user. The lower mounting member is substantially U-shaped and has a front face, a rear face, and upper and lower surface portions. The lower surface portions are adapted to be engaged with the lower dentitions of the user. The releasable fastening assembly are affixed to the lower and upper surface portions of the upper and lower mounting members, respectively.

12 Claims, 2 Drawing Sheets

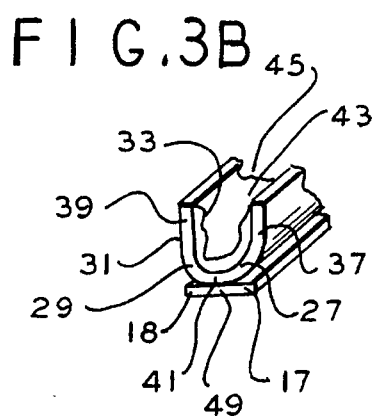
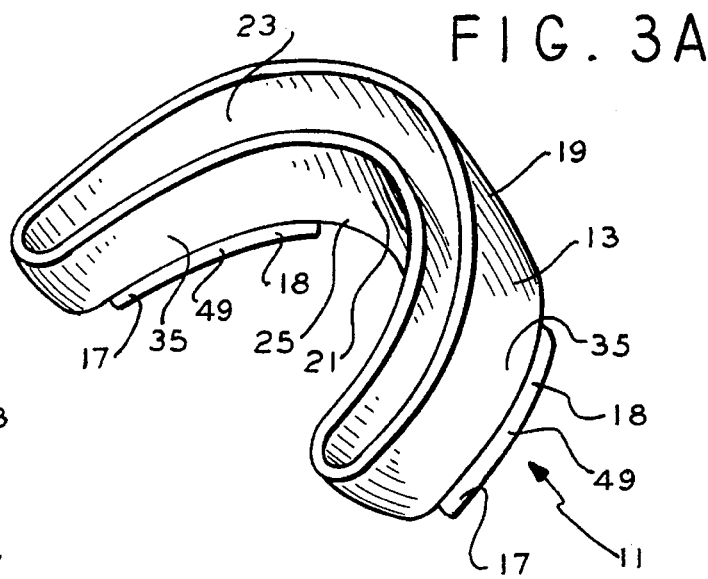
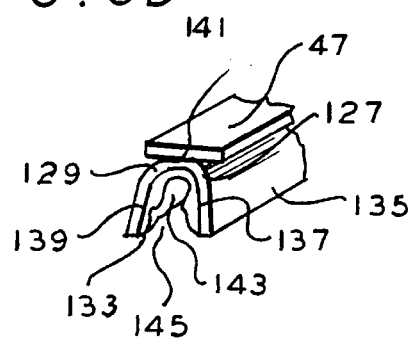
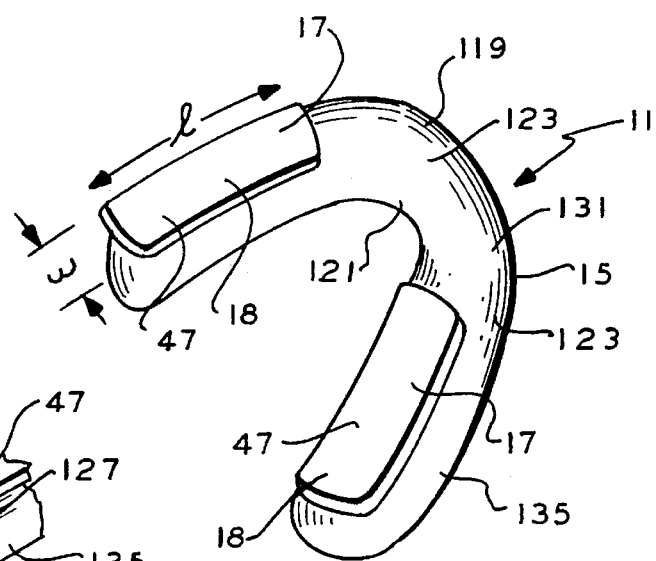

SNORING AND SLEEP APNEA DEVICE

This application is a continuation, of application Ser. No. 08/075,801, filed Jun. 14, 1993 abandoned.

FIELD OF THE INVENTION

This invention relates to devices which prevents interference with normal breathing during sleeping, and more particularly to a device which alleviates snoring and sleep apnea.

BACKGROUND OF THE INVENTION

Obstructive sleep apnea and obstructive breathing (snoring) is mainly caused by the collapse of the airway at the back of the throat. This occurs when the tongue falls to the back of the throat and blocks the airway. In snoring, the air forcibly passes, causing loud vibrations. In obstructive sleep apnea (OSA), the airway is completely blocked by the tongue and the patient cannot breathe at all. This condition exists for at least 10 seconds but can last up to 70–80 seconds. As the oxygen level in the blood begins to fall, the brain becomes alerted and eventually wakes up the patient—usually with a loud gasp, thrashing, and extreme vibrating noises. As soon as the patient's breathing returns to normal, the situation reoccurs, over and over again. This can occur 400–500 times a night, in severe cases.

DESCRIPTION OF THE PRIOR ART

Various devices for preventing or decreasing snoring are known in the prior art. STRICKLAND in U.S. Pat. No. 3,434,470 discloses an oral device to inhibit snoring wherein the device includes a plate adapted to be placed within the mouth in the U-shaped space defined by the upper teeth. The plate has mounting structure thereon which releasably grips the upper teeth, whereby the plate reduces the effective volume of the air flowing into and out of the mouth. The decreased air flow resulting from the presence of the plate inhibits snoring.

Shapiro et al in U.S. Pat. No. 5,117,816 discloses a device which comprises a mouthpiece formed from a moldable thermal-plastic material having an upper surface portion which substantially covers the entire maxillary (upper) dentition and a lower surface portion which contacts substantially the entire mandible (lower) dentition of a user's mouth. The lower surface portion includes a downwardly extending flange intended to extend into the lingual (tongue side of the teeth) vestibule of a user in order to maintain a forward posture of the lower jaw. An airway passage is centrally disposed to permit adequate breathing through the mouthpiece if nasal blockage is present. An interior portion of the mouthpiece, surrounding the airway passage, is concave in shape to enable proper positioning of a user's tongue. The device further utilizes a handle, preferably made from acrylic, used to aid in protecting the user during the initial fitting process. To assure the integrity of the airway slot during this fitting process, the handle includes a specially shaped extension portion which may be frictionally secured in the airway passage while the entire mouthpiece may be maneuvered by a remote upper portion of the handle.

Samelson in U.S. Pat. No. 4,304,277 discloses a device which is an integrally molded body. The device provides dental engaging portions and a rearwardly-opening central socket for cooperating with the forward portion of a user's tongue in a manner to draw the tongue forwardly so as to increase the unobstructed dimension of the nasal breathing passage. When operatively positioned within the mouth, some of the user's upper and lower teeth will enter into recesses provided by the device. The tongue will be held in the socket by a negative pressure developed in the socket. When the tongue is held, it draws the body of the tongue forwardly of its usual restive position behind the lower teeth and adjacent the soft palate, the uvula and the posterior pharyngeal wall, thereby increasing the dimension of the air flow passage through the naso-pharynx to facilitate nasal breathing.

Toone in U.S. Pat. No. 4,901,737 discloses a rigid, generally V-shaped wedge molded to the entire mandibular dentition and a portion of the maxillary dentition. It is completely open in the front, and open at the top (across the palatal arch). The mandibular incisal edge is embedded, with a lip extending about 1–2 mm over the labial surface of the mandibular incisors. It extends over the lingual surfaces of all mandibular teeth and downwardly into the lingual vestibule. It covers the palatal surfaces of the maxillary bicuspids and molars and extends onto the palate. The lack of full palatal coverage provides space for the tongue, which rests in its normal position. It comprises a pair of generally V-shaped spacer members disposed in a spaced apart, side by side relationship. In an adjustable embodiment, each of the spacer members are formed in two pieces, an upper and a lower portion. A threaded adjustment rod having one end disposed within one of the portions and a second end bearing against the other of the portions is used to adjust the relative positions of the upper and lower portions. The range of adjustment permitted by such adjustment rod is relatively limited.

The present invention provides a device which can prevent snoring and sleep apnea. The device is less bulky and has the advantage of being flexible, and adjustable to a degree that the above described prior art references were not. It also can be adjusted by the user, and it is of a much simpler design and is more comfortable than the prior art.

SUMMARY OF THE INVENTION

The present invention, in its broadest aspect, provides a device which can be molded to fit a particular user's mouth for the prevention of snoring and sleep apnea. It comprises an upper and lower mounting means and a releasable fastening means. The upper mounting means is substantially U-shaped and has a front face, a rear face, and upper and lower surface portions. The upper surface portions are adapted to be engaged with the upper dentitions of the user. The lower mounting means is substantially U-shaped and has a front face, a rear face, and upper and lower surface portions. The lower surface portions are adapted to be engaged with the lower dentitions of the user. The releasable fastening means are affixed to the lower and upper surface portions of both the upper and lower mounting means, respectively.

The present invention, in a narrower aspect, provides a device which can be molded to fit a particular user's mouth for the prevention of snoring. It comprises an upper and lower mounting means and a releasable fastening means. The upper mounting means is substantially U-shaped and has front and rear faces, and upper and lower surface portions, each surface portion having inner and outer edges. The upper mounting means comprises, an outer flexible member formed from a thermoplastic material such as that made by General Electric under the trademark LEXAN, an inner deformable member formed from another thermoplastic material such as that made by DuPont under the trademark ELVAX, and side and bight portions and inner and outer wall portions. The side portions has length and width. The inner and outer wall portions extend upwardly from the inner and outer edges of the upper surface portion. The bight portion interconnects the inner and outer wall portions. The inner and outer wall portions and said bight portion, are transversely U-shaped to define a tooth receiving groove having an open extremity, which groove is adapted to be engaged with the upper dentitions of a user. The lower mounting means is also substantially U-shaped and has front and rear faces, and upper and lower surface portions, each surface portion having inner and outer edges. The lower mounting means comprises, an outer flexible member, and side and bight portions and inner and outer wall portions. The side portions has length and width. The inner and outer wall portions extend downwardly from the inner and outer edges of the lower surface portion. The bight portion interconnects the inner and outer wall portions. The inner and outer wall portions, and said bight portion, are traversely U-shaped to define a tooth receiving groove having an open extremity, which groove is adapted to be engaged with the lower dentitions of a user. The releasable fastening means are formed by hook fastening material affixed to the lower and upper surface portions of the side portions of the upper and lower mounting means, respectively. The hook fastening material extends substantially the full length and width of said side portions.

It is an object of the present invention to provide an improved anti-snoring and sleep apnea device.

Another object of the present invention is to provide an anti-snoring and sleep apnea device which is of simple design.

A still further object of the present invention is to provide an anti-snoring sleep apnea device which permits a significant range of adjustment.

An additional object of the present invention is to provide an anti-snoring sleep apnea device which has shock absorbing capability, and which prevents teeth grinding and its deleterious effects.

Another object of the present invention is to provide an anti-snoring sleep apnea device that is therapeutic, in that it permits the jaw muscles to gradually accommodate to the required position of the device in the user's mouth during an adjustment period.

These and other objects and advantages of the invention will become clear from the following description of a preferred embodiment of the invention.

BRIEF DESCRIPTION OF THE DRAWINGS

FIG. 3A is a simplified perspective view of the upper mounting means, without its inner deformable member and hook portions of the fastening means of FIGS. 1A and 1B;

FIG. 3B is a fragmentary, simplified, cross-sectional, perspective view of a portion of the upper mounting means and hook portions of the fastening means of FIG. 3A;

FIG. 3C is a simplified perspective view of the lower mounting means and hook portions of the fastening means of FIGS. 2A and 2B; and FIG. 3D is a fragmentary, simplified, cross-sectional, perspective view of a portion of the lower mounting means and hook portion of the fastening means of FIG. 3C.

DETAILED DESCRIPTION OF THE INVENTION

Figure 1A:
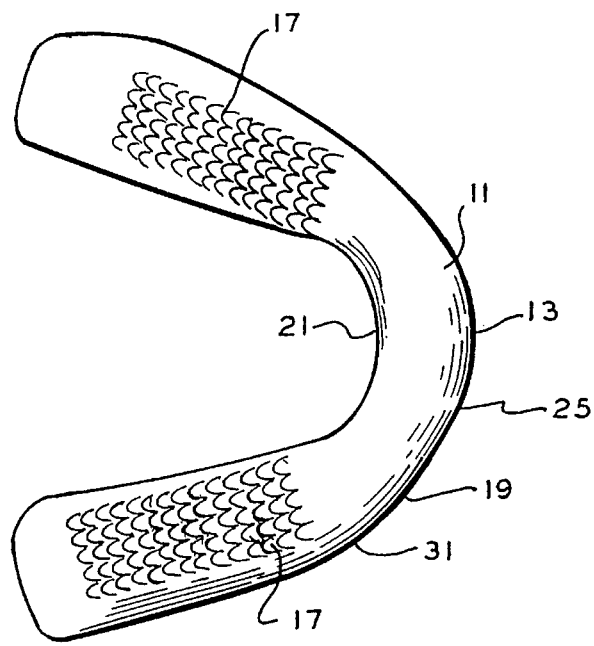
FIG. 1A is an enlarged bottom plan view of the upper mounting means and hook portions of the fastening means of the present invention.
Figure 1B:
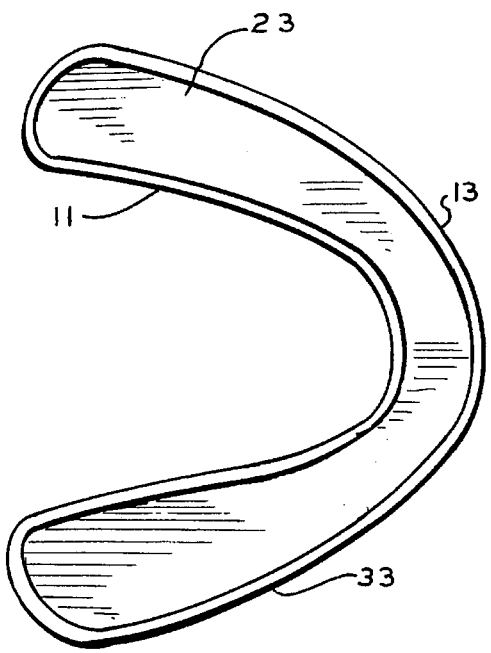
FIG. 1B is an enlarged top plan view of upper mounting means of FIG. 1A.
Figure 2A:
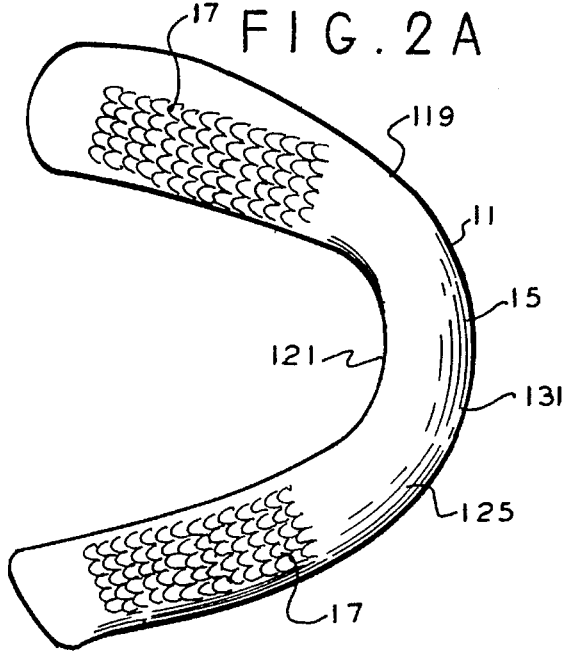
FIG. 2A is an enlarged top plan view of the lower mounting means and hook portions of the fastening means of the present invention.
Figure 2B:
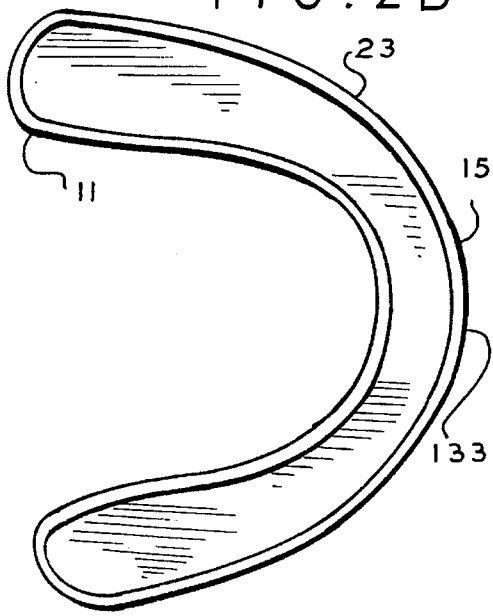
FIG. 2B is an enlarged bottom plan view of lower mounting means of FIG. 2A.

The device or appliance, which can be molded to fit a particular patient or user's mouth to prevent snoring sleep apnea, is generally designated by reference numeral 11. The device 11 comprises an upper mounting means 13, a lower mounting means 15 and a releasable fastening means 17. The upper mounting means 13 is substantially U-shaped and has front and rear faces, 19 and 21, respectively, upper and lower surface portions, 23 and 25, respectively, having inner and outer edges, 27 and 29, respectively. The upper mounting means 13 is a two layer structure comprising an outer flexible member 31 formed from a thermoplastic material such as that made by General Electric under the trademark LEXAN and an inner deformable member 33 formed from a thermoplastic material such as that made by DuPont under the trademark ELVAX. It further comprises a front portion 34 a pair of side portions 35, inner and outer wall portions, 37 and 39, respectively, and a bight portion 41. The inner and outer wall portions, 37 and 39, respectively, extend upwardly from the inner and outer edges, 27 and 29, respectively, of the upper surface portion 23. The bight portion 41 interconnects the inner and outer wall portions, 37 and 39, respectively. The inner and outer wall portions, 37 and 39, respectively, and the bight portion 41, are transversely U-shaped to define a tooth receiving groove 43 having an open end or extremity 45. The groove 43 is adapted to be engaged with the upper dentitions of a user. The lower mounting means 15 is substantially U-shaped and has front and rear faces, 119 and 121, respectively, having inner and outer edges, 127 and 129, respectively. The lower mounting means 15 also comprises a two layer structure, an outer flexible member 131 formed from a thermoplastic material such as made by General Electric under the trademark LEXAN and an inner deformable member 133 formed from a thermoplastic material such as made by DuPont under the trademark ELVAX. It further comprises a front portion 134 a pair of side portions 135, inner and outer wall portions, 137 and 139, respectively, and a bight portion 141. The inner and outer wall portions, 137 and 139, respectively, extend downwardly from the inner and outer edges, 127 and 129, respectively, of the upper surface portion 123. The bight portion 141 interconnects the inner and outer wall portions, 137 and 139, respectively. The inner and outer wall portions, 137 and 139, respectively, and the bight portion 141, also are transversely U-shaped to define a tooth receiving groove 143 having an open and or extremity 145. The groove 143 is adapted to be engaged with the lower dentitions of a user. The releasable fastening means 17 comprise two pairs of individual fasteners 18, which readily engage and disengage each other and which are preferably formed of opposing hook fastening materials. The hook fastening material of the individual fasteners 18 comprises a plurality of hook like members or hooks formed on its surface, which hooks comprise a narrow, flexible, elongated portion or stem with an end in the shape of a hemisphere, the curved portion extending outward. The preferred fastening material is the dual lock SUPERLOCK™ material sold by Radio Shack Corp. Another fastening material which could be used is the VELCRO® fasteners manufactured by Velcro U.S.A. Inc. These individual fasteners 18 are preferably affixed by heated glue material of the same material that the inner deformable member 33 is made of, or a conventional glue, to the lower and upper surface portions, 25 and 123, respectively, of the side portions 35 and 135, of the upper and lower mounting portions, 13 and 15, respectively. More specifically, the hook portions 47 of the lower fasteners 18 are affixed to the upper surface portions 123 of the side portions 135 of the lower mounting means 15. The hook portions 47 are disposed so as to extend the full length "l" and width "w" width of the Bite 41 of each of the side portions 135 (as is best seen in FIG. 3C). Similarly, the opposing hook portions 49 of the upper fasteners are affixed to the lower surface portions 25 of the side portions 35 of the upper mounting means 13. These opposing hook portions 49 are also disposed so as to extend the full length "l" and width "w" width of the Bite 141 of each of the side portions 35.

Because of the nature of the opposing hook fastening material forming the fastening means 17, and the flexibility of the entire upper and lower mounting means 13 and 15, it provides shock absorbing capability to the device 11. Furthermore, such shock absorbing capability prevents any teeth grinding thereby obviating the noises associated with it as well as the deleterious effects thereof. Also the range of adjustability of the lower mounting means 15 is relatively wide, permitting both forward and back movement, and/or left and right side movement. This is accomplished because of the nature of the fastening means 17 permit the individual fasteners 18 to be readily detached from one another and repositioned by the user (patient). Accordingly, adjustment is easily accomplished by the user, unlike the prior art devices. Additionally since the front and back portions of the lower jaw do not move together in a straight line nor in the same plane, the flexible nature of the fastening means 17 compensates for such non-rectilinear movement. Therapeutic value is provided by the device 11 since the fasteners 18 on the lower mounting means 15 permit it to be gradually moved forward over a period of days or weeks, to the required position for preventing snoring and sleep apnea. In this way the jaw muscles can be gradually trained so they comfortably adjust to the required position for preventing snoring and sleep apnea.

Accordingly, after the device 11 is made and fitted by the dentist, the user can immediately use it at home. If after using it at home, the user finds it uncomfortable, then the user can readjust it. This is accomplished by disengaging both mounting means 13 and 15 from each other and then moving the lower mounting means 15 backwards until it feels comfortable. Then, the user can move the lower mounting means 15 forward over a period of time until the final, proper, position is reached. Hence, the device is user adjustable at home, without having to return to the dentist's house.

The procedure for making the device or appliance 11 so that it fits properly in the patient or user's mouth is described as follows:

1. Impressions of the patient's upper and lower teeth are taken using a standard dental material called alginate.

2. A wax wafer approximately ½" thick and 1"long is placed on the lower back teeth on both left and right sides. The patient is guided into closing his teeth together, with his lower jaw positioned as far forward as possible. As the patient closes his mouth, he will bite into the wax wafer creating an imprint or registration in the wax wafer.

3. Plaster or dental stone is poured into the alginate impressions and allowed adequate time to set hard (approximately 20 min.). The hardened stone is removed from the impression creating an exact duplicate or model of the patient's upper and lower teeth.

4. The wax wafer is placed on the lower model and the upper model is positioned onto the wax wafer, thereby relating the two models in the exact same positions as the patient's teeth.

5. The models, with the wax wafer attached, are fastened onto a conventional articulator—an instrument with a hinge type action that will hold the models and wax wafer firmly in position and can simulate the patient's jaw movements.

6. The wax wafer is removed but the models are held in position by the articulator.

7. A different layer of wax having a high melting temperature is placed over all of the teeth of the upper model to act as a spacer or shim. A sheet made of the same material that the outer flexible member 31 is made of, is heated and molded around this wax. When cooled, the sheet is cut and smoothed to form the outer flexible member 31 portion of the upper tray or upper mounting means 13 that essentially fits the exact arch shape but is spaced or shimmed from the teeth. This step is repeated for the lower model to form the outer flexible member 31 portion of the lower mounting means 15.

8. The wax layer is removed. The formed portion 31 of the upper mounting means 13 is placed in position on the upper model, and the material which is made of the same material that the inner deformable member 33 is made of, is heated to a temperature sufficient for it to become a fluid. This fluid is injected into the formed portion 31 of the upper mounting means 13 and is forced around all of the teeth on the upper model. When this material cools, it will be formed around all of the teeth and forms the inner deformable member 33, which is attached to the outer tray or outer flexible member 31 potion of the upper mounting means 13. This step is repeated to form the outer flexible member portion of the lower mounting means 15.

9. The upper and lower mounting means, 13 and 15, respectively, are placed on the respective models which are related to each other on the articulator. The individual fasteners 18 of the releasable fastening means 17 are placed on the lower and upper surface portions, 25 and 123, respectively, of the upper and lower mounting means, 13 and 15, respectively, so that they approximate each other. The individual fasteners 18 are then glued to the upper and lower mounting means, 13 and 15, respectively, by heated glue material made of the same material that the inner deformable member 33 is made of or another glue, if desired. The preferable fastening means 17 utilized is the dual lock SUPERLOCK™ fastening material made by the RADIO SHACK Corporation, catalog number 64-2363. Alternatively, the individual fasteners 18 of the fastening means 17 can be imbedded into the mounting means 13 and 15 as they are formed in step 7, above. Another alternative is to have the fastening means 17 formed as projections while the mounting means 13 and 17 are formed. When cooled or dry, the device or appliance 11 is complete.

10. The appliance 11 is taken to the patient and the separate upper and lower mounting means, 13 and 15, respectively, are placed separately onto the teeth.

11. The patient is again guided to close his teeth, with the lower jaw as far forward as possible.

12. When the patient bites the individual fasteners 18 of the fastening means 17, they will attach to one another thereby holding the upper and lower mounting means, 13 and 15, respectively, together in this forward position and thereby holding the lower jaw in the forward position.

For convenience, the terms "upper" and "lower" are used in the appended claims in the sense that the device is installed on the upper and lower dentitions of a user.

13. If the desired position is not achieved, the mounting means, 13 and 15, respectively, are simply separated and the above procedure repeated until satisfied.

The appliance or device 11 brings the patient's lower jaw forward. The tongue is attached to the lower jaw and therefore is also brought forward. The process of bringing the tongue and jaw forward causes the airway to open—preventing snoring and sleep apnea. It is purely a mechanical procedure that works immediately and will revert to obstruction as soon as the appliance or device 11 is removed. The appliance or device 11 must be worn continuously during sleep to provide the above benefits.

Although the present invention has been described and illustrated with respect to a preferred embodiment; it is not to be so limited since modifications and changes can be made therein which are within the full intended scope of the invention.

Having described this invention what is sought to be protected by Letters Patent is set forth in the following claims:

1. A device which can be molded to fit a particular user for preventing interference with normal breathing during sleeping comprising:

a substantially U-shaped upper mounting means having a front face, a rear face, and upper and lower surface portions, said, upper surface portions adapted to be engaged with the upper dentitions of said user;

a substantially U-shaped lower mounting means having a front face, a rear face, and upper and lower surface portions, said lower surface portions adapted to be engaged with lower dentitions of said user; and releasable fastening means affixed to said lower and upper surface portions of said upper and lower mounting means, respectively, wherein said releasable fastening means are formed of a plurality of interconnecting members, comprising a plurality of interlocking fastening members.

2. The device according to claim 1, wherein each of said upper and lower mounting means have side portions, and wherein said fastening means are affixed to said side portions of upper and lower mounting means.

3. The device according to claim 2, wherein said fastening means extend a portion of the length of said side portions of said upper and lower mounting means.

4. The device according to claim 2, wherein said fastening means extend a portion of the bight width of said lower and upper surface portions of said side portions of said upper and lower mounting means, respectively.

5. The device according to claim 3, wherein said upper mounting means comprises inner and outer wall portions extending upwardly from inner and outer edges of said lower surface portion, and inner and outer wall portions extending downwardly from said inner and outer edges of said upper surface portion.

6. The device according to claim 5, wherein each of said upper and lower mounting means has a bight portion which interconnects said inner and outer wall portions of each of said upper and lower mounting means.

7. The device according to claim 6, wherein said bight portion and inner and outer wall portions of each of said upper and lower mounting means being transversely U-shaped to define an arcuate, tooth-receiving groove having an open extremity.

8. The device according to claim 3, wherein each of said upper and lower mounting means comprises an outer flexible member and an inner deformable member.

9. The device according to claim 3, wherein when said user disposes said upper and lower mounting means on said upper and lower teeth and then moves said user's mouth, said releasable fastening means on said upper and lower mounting means engage each other and maintain said user's lower jaw in its forward position.

10. The device according to claim 3, wherein said outer flexible member and said inner deformable member are formed of thermoplastic materials.

11. The device according to claim 3, wherein said releasable fastening means are adjustable.

12. A device which can be molded to fit a particular user's mouth for preventing interference with normal breathing during sleeping comprising:

A. a substantially U-shaped upper mounting means having, front and rear faces, and upper and lower surface portions, each having inner and outer edges, comprising;

i) an outer flexible member formed of a thermoplastic material, ii) an inner deformable member formed of a thermoplastic material, iii) side portions having length and width, iv) inner and outer wall portions extending downwardly from said inner and outer edges of said upper surface portion, v) a bight portion which interconnects said inner and outer wall portions, said inner and outer wall portions and said bight portion being transversely U-shaped to define a tooth receiving groove having an open extremity, said groove adapted to be engaged with the upper dentitions of said user, B. a substantially U-shaped lower mounting means having, front and rear faces, and upper and lower surface portions, each having inner and outer edges, comprising;

i) an outer flexible member formed of a thermoplastic material, ii) an inner deformable member formed of a thermoplastic material, iii) side portions having length and width, iv) inner and outer wall portions extending upwardly from said inner and outer edges of said lower surface portion, v) a bight portion which interconnects said inner and outer wall portions, said inner and outer wall portions and said bight portion being transversely U-shaped to define a tooth receiving groove having an open extremity, said groove adapted to be engaged with the lower dentitions of said user, and C. releasable fastening means formed of a plurality of interlocking fastening members affixed to said lower and upper surface portions of said side portions of said upper and lower mounting means, respectively, and extending along a portion of said length and a portion of said bight width of both said side portions.

\* \* \* \* \*